United States Patent
Govindappa et al.

(10) Patent No.: US 9,862,958 B2
(45) Date of Patent: Jan. 9, 2018

(54) NUCLEOTIDE SEQUENCE AND A PROCESS THEREOF

(71) Applicant: Biocon Limited, Bangalore (IN)

(72) Inventors: Nagaraj Govindappa, Bangalore (IN); Sankar Periyasamy, Tirupur (IN); Shivakumar Madenahalli Channabasappa, Bangalore (IN); Suma Sreenivas, Bangalore (IN); Kedamath Nanjund Sastry, Bangalore (IN)

(73) Assignee: Biocon Limited, Bangalore (IN)

( * ) Notice: Subject to any disclaimer, the term of this patent is extended or adjusted under 35 U.S.C. 154(b) by 273 days.

(21) Appl. No.: 14/434,595

(22) PCT Filed: Dec. 5, 2012

(86) PCT No.: PCT/IB2012/056985
§ 371 (c)(1),
(2) Date: Apr. 9, 2015

(87) PCT Pub. No.: WO2014/057315
PCT Pub. Date: Apr. 17, 2014

(65) Prior Publication Data
US 2015/0284731 A1    Oct. 8, 2015

(30) Foreign Application Priority Data
Oct. 10, 2012 (IN) ............ 4231/CHE/2012

(51) Int. Cl.
*C12P 21/00* (2006.01)
*C12N 15/81* (2006.01)
*C12P 19/34* (2006.01)
*C07K 14/76* (2006.01)
*C07K 14/81* (2006.01)
*C12N 9/04* (2006.01)
*C12P 21/02* (2006.01)

(52) U.S. Cl.
CPC ............ *C12N 15/815* (2013.01); *C07K 14/76* (2013.01); *C07K 14/811* (2013.01); *C12N 9/0006* (2013.01); *C12P 19/34* (2013.01); *C12P 21/00* (2013.01); *C12P 21/02* (2013.01); *C12Y 101/01014* (2013.01)

(58) Field of Classification Search
None
See application file for complete search history.

(56) References Cited

PUBLICATIONS

McGonigal et al. Construction of a Sorbitol-Based Vector for Expression of Heterologous Proteins in *Saccharomyces cerevisiae*. Applied and Environmental Microbiology, Feb. 1998, p. 793-794.*

* cited by examiner

*Primary Examiner* — Kagnew H Gebreyesus
(74) *Attorney, Agent, or Firm* — Schwegman Lundberg & Woessner, P.A.

(57) ABSTRACT

The present disclosure relates to a process of identification and isolation of sorbitol dehydrogenase promoter from *Pichia pastoris*. Further, the present disclosure also relates to expression of heterologous proteins under the control of Sorbitol dehydrogenase promoter in *Pichia pastoris*.

8 Claims, 6 Drawing Sheets

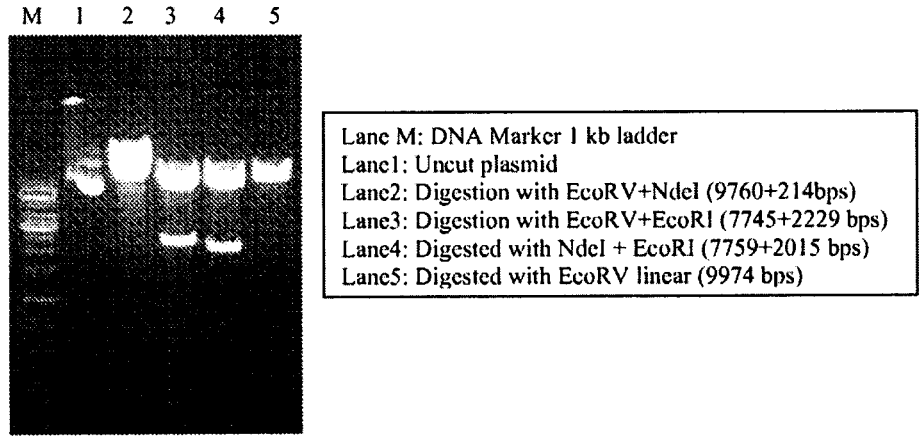
Figure 1: Restriction analysis of SDPHA/pMBL208.
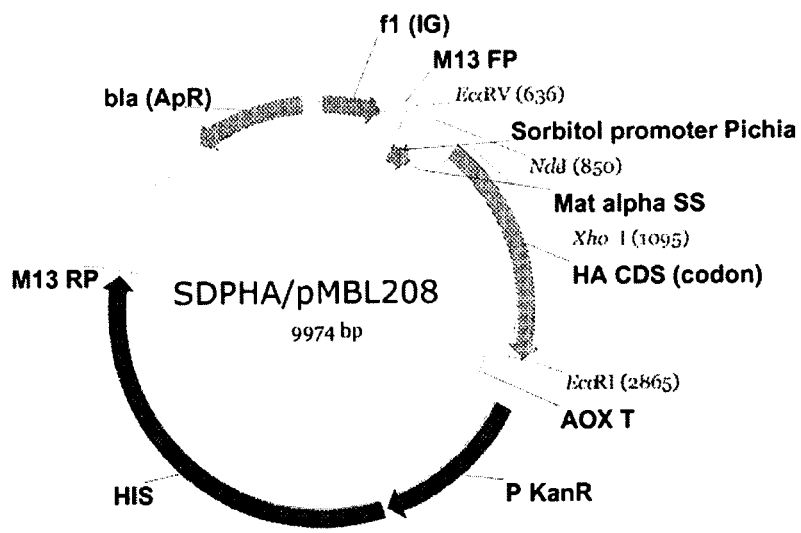
Figure 2: Vector map of SDPHA/pMBL208

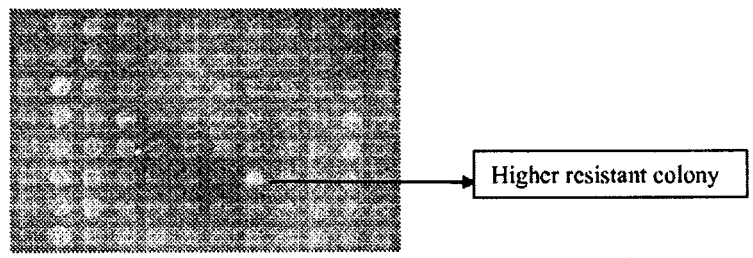
Figure 3: Screening of colonies for selecting high producer of recombinant protein on G418 antibiotic.
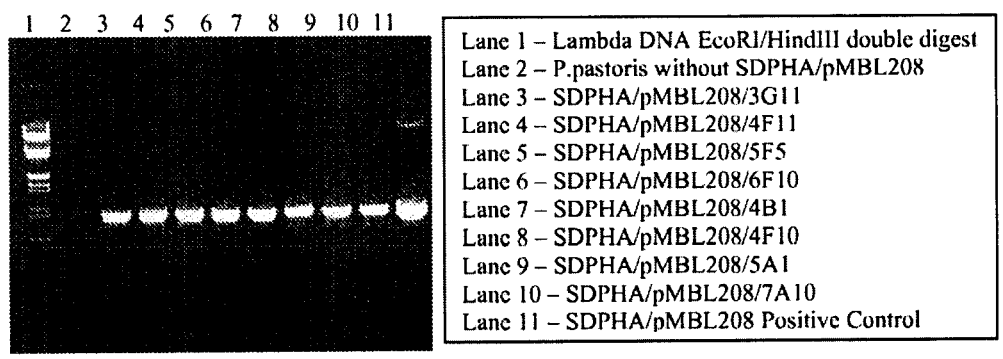
Figure 4: PCR confirmation of the integrated gene into the *P.pastoris* genome.
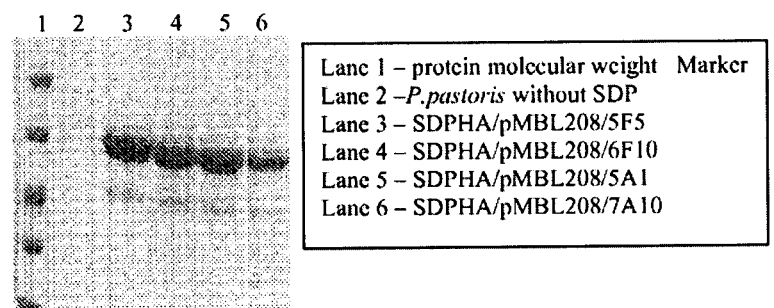
Figure 5: Expression analysis of HA when grown using sorbitol as a sole carbon source

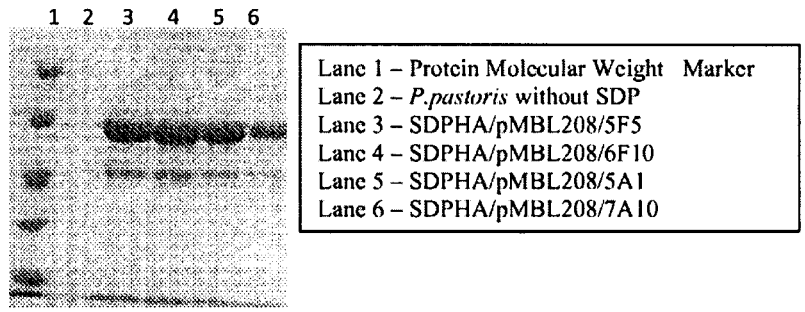
Figure 6: Expression analysis of HA when grown using methanol as a sole carbon source
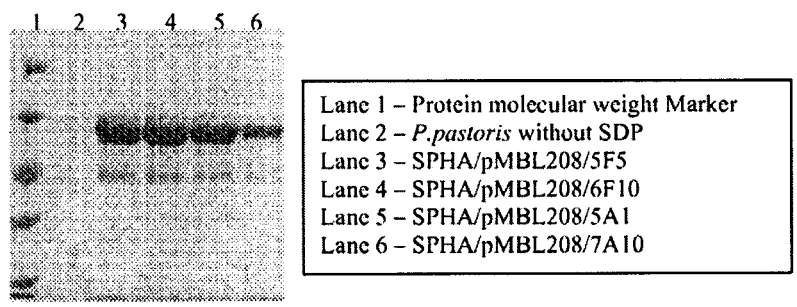
Figure 7: Expression analysis of HA when grown using glucose as a sole carbon source
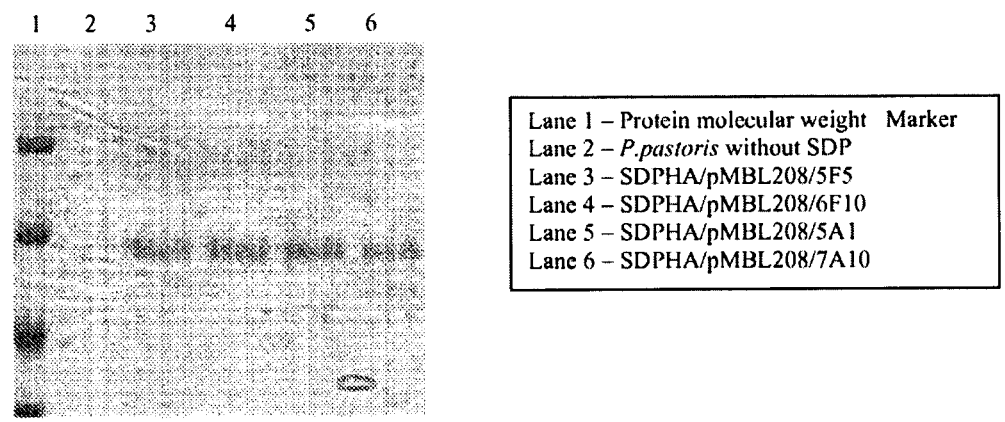
Figure 8: Expression analysis of cell free supernatant without any induction(cells were grown in expansion medium)

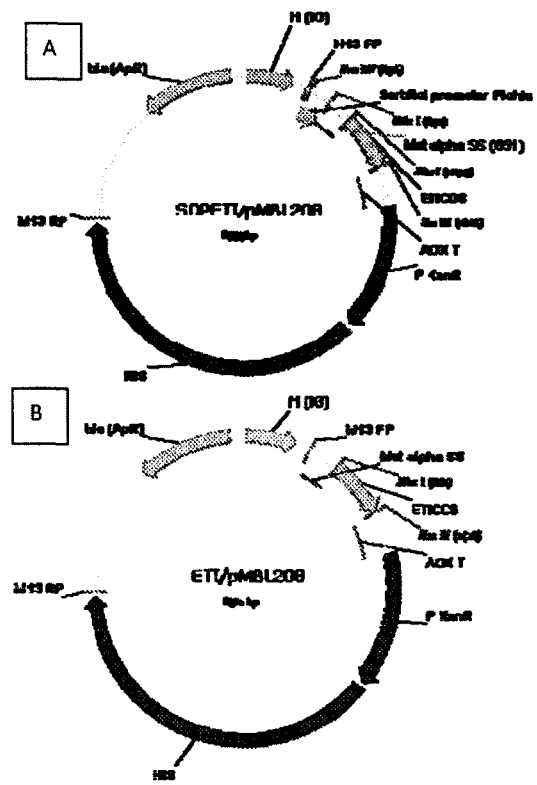

Figure 9: Picture of ETI expression constructs; A) ETI is cloned in the XhoI and E.coRI restriction sites under the control of sorbitol dehydrogenase promoter. B) ETI with no promoter upstream

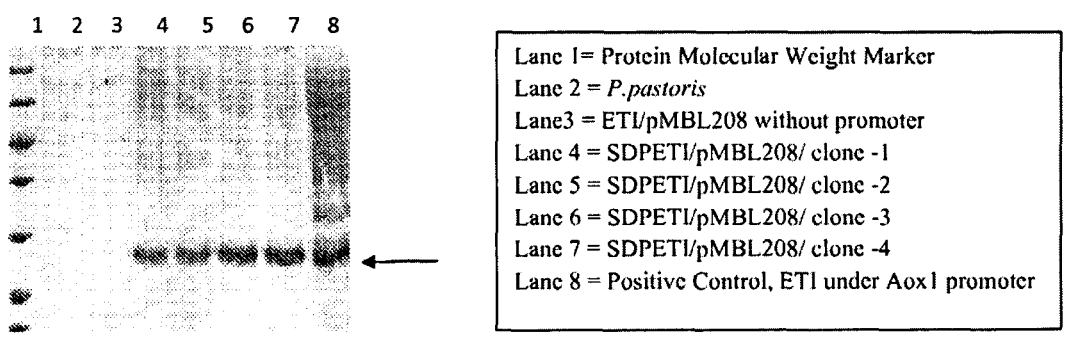

Lane 1= Protein Molecular Weight Marker
Lane 2 = *P.pastoris*
Lane3 = ETI/pMBL208 without promoter
Lane 4 = SDPETI/pMBL208/ clone -1
Lane 5 = SDPETI/pMBL208/ clone -2
Lane 6 = SDPETI/pMBL208/ clone -3
Lane 7 = SDPETI/pMBL208/ clone -4
Lane 8 = Positive Control, ETI under Aox1 promoter

Figure 10: Expression analysis of ETI when grown using sorbitol as a sole carbon source

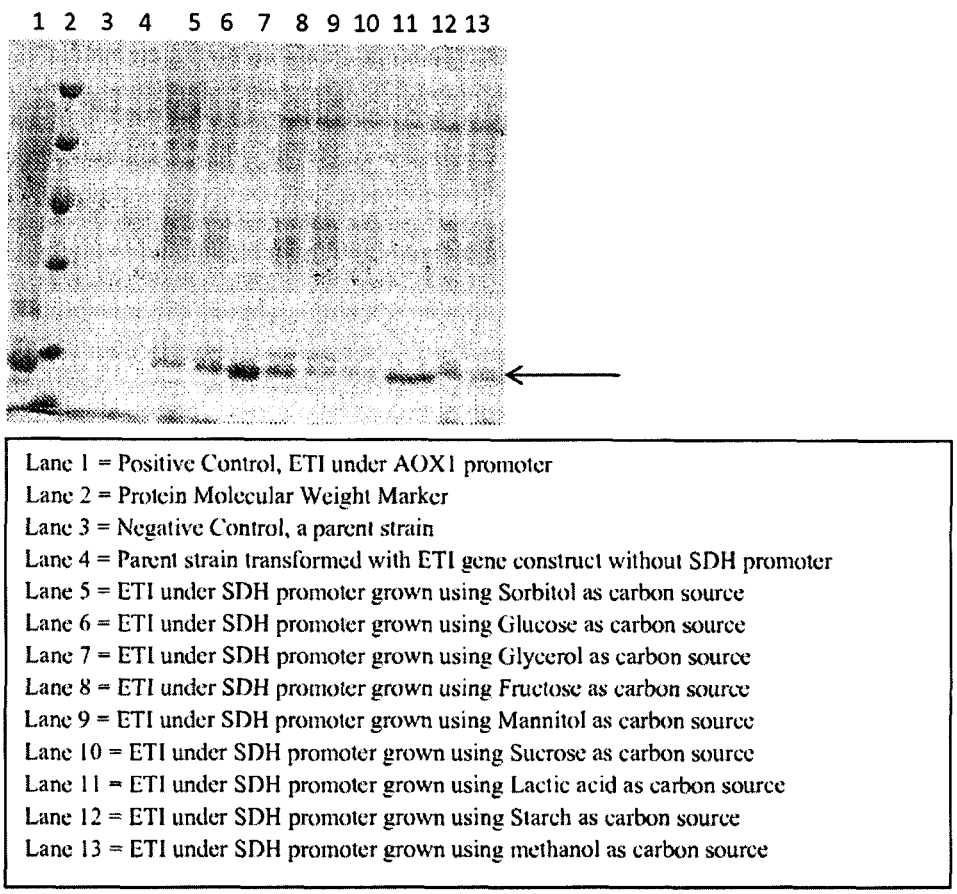
Fig. 11: Determination of ETI productivity under different carbon sources

SEQUENCE LISTING

<160> NUMBER OF SEQ ID NOS: 3

<210> SEQ ID NO 1
<211> LENGTH: 213
<212> TYPE: DNA
<213> ORGANISM: Pichia pastoris

```
-continued

<400> SEQUENCE: 1
aagttgtata ttattaatgg cggggcagaa tgctctcagt ctcaactttt gatgattgcc         60
gggattaaaa aatcatgcac accggaaaaa cttatcccaa atgtatgtac cccacgtaat        120
ccgttgtagt tccaccaaag aatttaaaac gtacttcccg cccaataatc tgttcccttt        180
cccgcttcat tacactcact attatccaac atg                                     213

<210> SEQ ID NO 2
<211> LENGTH: 34
<212> TYPE: DNA
<213> ORGANISM: Pichia pastoris
<220> FEATURE:
<221> NAME/KEY: primer_bind
<222> LOCATION: (1)..(34)

<400> SEQUENCE: 2
agatatcaag ttgtatatta ttaatggcgg ggca                                    34

<210> SEQ ID NO 3
<211> LENGTH: 30
<212> TYPE: DNA
<213> ORGANISM: Pichia pastoris
<220> FEATURE:
<221> NAME/KEY: primer_bind
<222> LOCATION: (1)..(30)

<400> SEQUENCE: 3
tcatatgttg gataatagtg agtgtaatga                                         30
```

NUCLEOTIDE SEQUENCE AND A PROCESS THEREOF

PRIORITY APPLICATIONS

This application is a U.S. National Stage Filing under 35 U.S.C. 371 from International Application No. PCT/IB2012/056985, filed on 5 Dec. 2012, and published as WO/2014/057315 on 17 Apr. 2014, which claims the benefit under 35 U.S.C. 119 to Indian Application No. 4231/CHE/2012, filed on 10 Oct. 2012; which applications and publication are incorporated herein by reference in their entirety.

TECHNICAL FIELD

The present disclosure describes identification and isolation of sorbitol dehydrogenase promoter from *P. pastoris* and expression of heterologous protein in *P. pastoris* under the influence of said isolated promoter, specifically expression of Human Albumin (HA) and *Erythrina* Trypsin Inhibitor (ETI).

BACKGROUND AND PRIOR ART OF THE DISCLOSURE

*Pichia pastoris* is a very widely used well-established industrial host for producing therapeutic recombinant proteins. Production of therapeutic recombinant proteins poses several problems such as clipping at N-terminal (Prabha et. al. 2009) or C-terminal, introduction of desired glycoforms (Wouter Vervecken et. al. 2004). There is a need for enhancing the protein productivity and quality to meet the growing demands of the market and the growing regulatory issues on biosimilarities. This can be achieved by co-expressing the molecular chaperones (Wei Zhang et. al. 2006), Co-expression of proteases to get the desired end product. In all these cases there is need for additional promoters for carrying out genetic manipulation to improve quality and quantity of the recombinant protein.

U.S. Pat. No. 6,033,898 discloses a DNA segment isolated from a *Saccharomyces cerevisiae* sorbitol dehydrogenase gene which is utilized to increase production of a heterologous polypeptide. U.S. Pat. No. 5,139,936 discloses a cloning vector containing a foreign gene and the yeast galactosidase (GAL1) regulatory region and promoter in position to increase expression of the foreign gene. U.S. Pat. No. 5,089,398 discloses the use of the promoter region from the glyceraldehyde-3-phosphate dehydrogenase to control expression of a foreign polypeptide in yeast.

Although several promoters, either constitutive or inducible are available for the *Pichia* expression system, AOX1 is employed in most studies and application. AOX1 promoter is a strong inducible promoter and has tight regulation by carbon sources, expression is highly repressed when *Pichia pastoris* is grown in the presence most of other carbon sources other than Methanol. Methanol is an inducer of AOX1 promoter, methanol is a hazardous substance due to its high flammability and toxicity, also the cells growing on methanol have a very high oxygen consumption which usually requires addition of pure oxygen to the culture, thus increasing the cost of the process and limiting the cultivation capacity at large scale (Monika Bollok et. al., Recent Patents on biotechnology, 3(2009) 192-201.)

Also host cellular protein (HCP) release from *P. pastoris* grown on methanol is high which is mainly derived during cell lysis but it occurs to a much lower extent upon growth with glucose as a carbon source. As a result cells maintain higher viability and higher purity of the secreted protein.

Further, the sorbitol dehydrogenase promoter identified in *S. cerevisiae* is 750 bps. Due to large base pair size, it is not so easy to carry out genetic manipulation as it leads to increase of the vector size. The instant disclosure aims at overcoming the issues mentioned above. Also, there is a need in the art to identify more promoters for the expression of heterologous recombinant proteins in *Pichia pastoris* which does not require any specific induction for expression of protein.

SUMMARY OF THE DISCLOSURE

Accordingly, the present disclosure relates to a nucleotide sequence set forth as SEQ ID No.1; a process of isolation of SEQ ID No.1, said process comprising acts of—a) isolating genomic DNA from *P. pastoris*, b) amplifying a region comprising SEQ ID No.1 within the isolated genomic DNA, and c) subjecting the amplified product to a conventional gel elution procedure to isolate said SEQ ID No.1; a process of expressing a gene under regulation of SEQ ID No.1 in a medium comprising non-specific inducer, said process comprising acts of—a) cloning said gene in an expression construct downstream to the SEQ ID No.1, b) transforming a host with the expression construct, and c) expressing the gene under the regulation of said SEQ ID No.1 in a medium comprising non-specific inducer for production of heterologous protein; a vector comprising the nucleotide sequence as mentioned above; a transformed host cell comprising the vector as mentioned above.

BRIEF DESCRIPTION OF ACCOMPANYING FIGURES

FIG. 1 shows restriction analysis of SDPHA/pMBL208. All the digestions results in the expected pattern.

FIG. 2 shows vector map of SDPHA/pMBL208.

FIG. 3 shows screening of colonies for selecting high producer of recombinant protein on G418 antibiotic. The colony shown in the arrow indicates the higher resistant clone.

FIG. 4 shows PCR confirmation of the integrated gene into the *P. pastoris* genome. All the clones selected are found to have the gene of interest.

FIG. 5 shows expression analysis of HA when grown using sorbitol as a sole carbon source.

FIG. 6 shows expression analysis of HA when grown using methanol as a sole carbon source.

FIG. 7 shows expression analysis of HA when grown using glucose as a sole carbon source.

FIG. 8 shows expression analysis of cell free supernatant without any induction (cells are grown in expansion medium).

Figure 12:
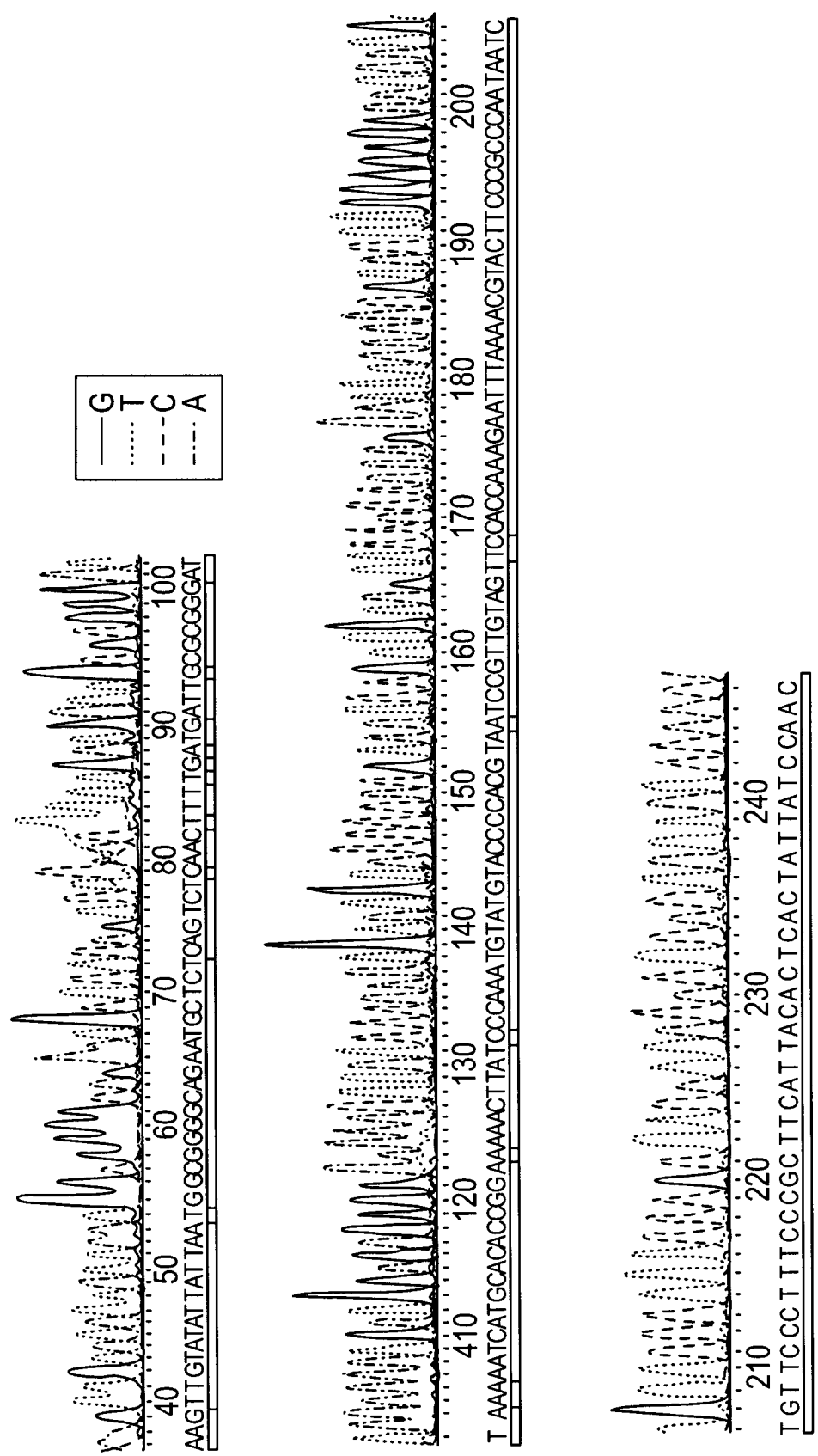

FIG. 9 shows Picture of ETI expression constructs; A) ETI is cloned in the XhoI and E.coRI restriction sites under the control of sorbitol dehydrogenase promoter. B) ETI with no promoter upstream.

FIG. 10 shows expression analysis of ETI when grown using sorbitol as a sole carbon source.

FIG. 11 shows determination of ETI productivity under different carbon sources.

FIG. 12 provides a chromatogram shows the sequencing results obtained for sorbital dehydrogenase promoter isolated from *P. pastoris*.

DETAILED DESCRIPTION OF DISCLOSURE

The present disclosure relates to a nucleotide sequence set forth as SEQ ID No. 1.

In an embodiment of the present, said nucleotide sequence is sorbitol dehydrogenase promoter.

In another embodiment of the present disclosure, said nucleotide sequence is identified and isolated from *P. pastoris*.

The present disclosure relates to a process of isolation of SEQ ID No.1, said process comprising acts of: a) isolating genomic DNA from *P. pastoris*, b) amplifying a region comprising SEQ ID No.1 within the isolated genomic DNA, and c) subjecting the amplified product to a conventional gel elution procedure to isolate said SEQ ID No.1.

In an embodiment of the present disclosure, the amplification of SEQ ID No.1 is carried out by forward primer set forth as SEQ ID No.2 and reverse primer set forth as SEQ ID No.3.

The present disclosure relates to a process of expressing a gene under regulation of SEQ ID No.1 in a medium comprising non-specific inducer, said process comprising acts of: a) cloning said gene in an expression construct downstream to the SEQ ID No.1, b) transforming a host with the expression construct, and c) expressing the gene under the regulation of said SEQ ID No.1 in a medium comprising non-specific inducer for production of heterologous protein.

In an embodiment of the present disclosure, said host is methylotrophic yeast, preferably *P. pastoris*.

In another embodiment of the present disclosure, said heterologous protein is selected from a group comprising human albumin and *erythrina* trypsin inhibitor.

In yet another embodiment of the present disclosure, said expression is carried out by a non-specific inducer.

In still another embodiment of the present disclosure, said non-specific inducer selected from a group comprising sorbitol, glucose, glycerol, fructose, mannitol, lactic acid, sucrose, starch, methanol or any combination thereof.

The present disclosure relates to a vector comprising the nucleotide sequence as mentioned above.

The present disclosure relates to a transformed host cell comprising the vector as mentioned above.

The present disclosure relates to identification of sorbitol dehydrogenase promoter as a potential tool to express heterologous recombinant proteins in *P. pastoris* that does not require any specific induction for expression.

In an embodiment of the present disclosure, 210 bps promoter is located on the chromosome 1 of *P. pastoris*.

In another embodiment of the present disclosure, sortibol dehydrogenase promoter is the smallest promoter in *P. pastoris*.

In an embodiment of the present disclosure, promoter region available upstream of Sorbitol dehydrogenase gene is identified to have CAAT and GC boxes within that region.

In another embodiment of the present disclosure, the promoter is successfully used to express recombinant proteins such as Human Albumin (HA) and *Erythrina* Trypsin Inhibitor (ETI).

In another embodiment of the present disclosure, the heterologous proteins such as human albumin and *erythrina* trypsin inhibitor are expressed under the control of sorbitol dehydrogenase promoter.

In another embodiment of the present disclosure, the sorbitol dehydrogenase promoter enables the expression of heterologous proteins under any type of carbon source.

In another embodiment of the present disclosure, the sorbitol dehydrogenase promoter enables the expression of heterologous protein utilizing sorbitol, glucose, glycerol, fructose, mannitol, lactic acid, sucrose, starch and methanol as a carbon source.

In another embodiment of the present disclosure, the sorbitol dehydrogenase gene from *P. pastoris* is identified by the following process: a) Sorbitol dehydrogenase gene orthologs is subjected to NCBI blast which resulted in multiple hits; b) identifying sorbitol dehydrogenase gene in *Pichia pastoris* located on the chromosome 1, and; c) analysing the sequence upstream of the identified sorbitol dehydrogenase gene.

In another embodiment of the present disclosure, expression of a target gene to obtain a protein of interest under the influence of the chimeric promoter of the instant invention is not limited by the carbon source being employed. In other words, by making use of the chimeric promoter of this invention, the protein of interest may be expressed by making use of any carbon source such as but not limited to sorbitol, glucose, glycerol, fructose, mannitol, lactic acid, sucrose. However, a person skilled in the art will recognize the most potent inducers for higher expression of a specific type of protein and hence will be able to employ any inducer having such high potency or likeliness of higher expression than the remaining inducers.

In another embodiment of the present disclosure the term non-specific inducer and carbon source is used interchangeably in accordance to the description.

In another embodiment of the present disclosure, recombinant expression system is selected from prokaryotic and eukaryotic hosts. Eukaryotic hosts include yeast cells (e.g., *Saccharomyces cerevisiae* or *Pichia pastoris*), mammalian cells or plant cells. Bacterial and eukaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells. The choice of the expression system depends on the features desired for the expressed polypeptide.

In another embodiment of the present disclosure, the most preferred host cells are methylotrophic yeasts. Strains of a methylotrophic yeast which can be modified using the present disclosure include, but are not limited to yeast strains capable of growing on methanol, such as yeasts of the genera *Pichia, Candida, Hansenula,* or *Torulopsis*. Preferred methylotrophic yeasts are of the genus *Pichia*. Methylotrophic yeast strains which can be modified using the present methods also include those methylotrophic yeast strains which have been engineered to express one or more heterologous proteins of interest.

In another embodiment of the present disclosure, the term "promoter" is used in the normal sense of the art, e.g. an RNA polymerase binding site. The term "vector" includes expression vectors, replicable vectors, transformation vectors and shuttle vectors, including vector combinations thereof.

In another embodiment of the present disclosure, the term "expression vector" means a construct capable of in-vivo or in-vitro expression.

In another embodiment of the present disclosure, preferentially the expression vector is incorporated in the genome of the organism. The term "incorporated" preferably covers stable incorporation into the genome.

In another embodiment of the present disclosure, "expressing polypeptides" is meant as expression of DNA sequences encoding the polypeptide. "Polypeptides" are polymers of [alpha]-amino acids which are covalently linked through peptide bonds. Polypeptides include low molecular weight polymers as well as high molecular weight polymers more commonly referred to as proteins. In addition, a polypeptide can be a phosphopolypeptide, glycopolypeptide or metallopoly-peptide. Further, one or more polymer chains may be combined to form a polypeptide. As used herein a "heterologous polypeptide" is a polypeptide which is not normally expressed and secreted by the filamentous fungus used to express that particular polypeptide. Heterologous polypeptides include polypeptides derived from prokaryotic sources (e.g., [alpha]-amylase from *Bacillus* species, alkaline protease from *Bacillus* species, and various hydrolytic enzymes from *Pseudomonas*, etc.), polypeptides derived from eukaryotic sources (e.g., bovine chymosin, human tissue plasminogen activator, human growth hormone, human interferon, urokinase, human serum albumin, factor VIII etc.), and polypeptides, derived from fungal sources other than the expression host (e.g., glucoamylase from *A. niger* and Heterologous polypeptides also include hybrid polypeptides which comprise a combination of partial or complete polypeptide sequences derived from at least two different polypeptides each of which may be homologous or heterologous with regard to the fungal expression host. Examples of such hybrid polypeptides include: 1) DNA sequences encoding prochymosin fused to DNA sequences encoding the *A. niger* glucoamylase signal and pro sequence alone or in conjunction with various amounts of amino-terminal mature glucoamylase codons, and 2) DNA sequences encoding fungal glucoamylase or any fungal carboxy protease, human tissue plasminogen activator or human growth hormone fused to DNA sequences encoding a functional signal sequence alone or in conjunction with various amounts of amino-terminal propeptide condons or mature codons associated with the functional signal.

The invention is further illustrated by the following examples. The following examples are provided for illustrative purposes only and are not intended to limit the scope of the invention.

EXAMPLES

Example 1: *Pichia pastoris* Sorbitol Dehydrogenase Promoter (SDP) Isolation and Cloning The coding sequence of sorbitol dehydrogenase gene is identified, which is located on chromosome no. 1 of *P. pastoris*. The region upstream to 5' region to the coding sequence of the identified gene is examined. The examined gene is identified as a promoter region for Sorbitol dehydrogenase comprising 210 bp. The genomic DNA of *P. pastoris* is isolated using the conventional gene isolation technique. The isolated gene is subjected to polymerase chain reaction to amplify the examined 210 bp region.

The primers used to amplify the examined gene are—

SORFP = 5' AGA TAT CAA GTT GTA TAT TAT TAA TGG CGG GGC A 3' (EcoRV at 5' end)

SORRP = 5' TCA TAT GTT GGA TAA TAG TGA GTG TAA TGA 3' (NdeI at 5'end).

The chromatogram presented in FIG. 12 shows the sequencing results obtained for sorbital dehydrogenase promoter isolated from *P. pastoris*. The promoter region from the region 37 to 246 bp is highlighted with brackets.

The amplicon is subjected to agarose gel electrophoresis against a suitable marker. The amplified 210 bp region on the gel is eluted using Qiagen spin columns. The gel purified product is A-tailed under the polymerase chain reaction. The A-tailed PCR product is ligated to TA vector (pTZ57R) at 16° C., overnight. The ligated product is transformed to *E. coli* DH5α by heat shock method and plated on LBA100 and incubated the plates at 37° C. overnight.

Example 2: Cloning and Restriction Analysis of SDPHA/pMBL208

The plasmid pMBL208 having human albumin gene (HA) with an AOX1 promoter is selected. The AOX1 promoter is removed from rHA/pMBL His plasmid by digesting it with EcoRV and NdeI restriction enzymes. Same restriction enzymes are used to release the sorbitol dehydrogenase promoter (SDP) from pTZ57R. The released SDP is ligated to the AOX1 removed vector (FIG. 2). The ligated product is transformed to *E. coli* DH5α and plated on LBA100, plates are incubated overnight at 37° C., and the transformed colonies are screened for correct plasmid by colony PCR. The positive clone is isolated and inoculated in Luria Broth (LB) and grown overnight at 37° C. to isolate plasmid, plasmid is isolated from overnight grown culture using Qiagen mini prep spin columns. Isolated plasmid is confirmed by restriction digestion (FIG. 1) with the following restriction enzymes—EcoRV and NdeI, EcoRV and EcoRI, EcoRI and NdeI and EcoRV.

Example 3: Transformation of *P. pastoris* with SDPHA/pMBL208

The plasmid SDPHA/pMBL208 is linearized with EcoRV and transformed to *P. pastoris*. The transformed cells are spread on to Yeast nitrogen base (YNB) agar plates without any amino acids for selection. The plates are incubated at 30° C. for two days till the colonies appear.

Example 4: Screening of Colonies for Higher Geneticin (G418) Resistance

Upon observing growth of the colonies in YNB agar plates, the colonies are picked and inoculated into Yeast Extract Peptone Dextrose (YPD) in 96-well plate and incubated at 30° C., overnight. The cultures from 96-well plate are stamped onto YPD agar plates containing 0.5 mg/ml of G418 and incubated the plated at 30° C. for 2 days. After 2 days the colonies showing higher resistance to G418 are selected and streaked onto YPD agar plates as shown in FIG. 3. The colony shown in the arrow indicates the higher resistant clone.

The clones selected based on their resistance to G418 are: 3G11, 4F11, 5F5, 6F10, 4B1, 4F10, 5A1, 7A10. From these selected clones, the genomic DNA is isolated by the Phenol Chloroform Method. The vector SDPHA/pMBL208 recombination is confirmed by PCR using the primers SORFP and HSAintRP. This gives amplification of about 750 bps (FIG. 4). FIG. 4 represents a gel for the PCR confirmation of the integrated gene into the *P. pastoris* genome for the clones 3G11, 4F11, 5F5, 6F10, 4B1, 4F10, 5A1, 7A10 and it was observed that all the clones had proper intergration of gene in to the host genome.

Example 5: Expression Studies in SDPHA/*P. pastoris*

The shake flask induction studies is carried out for 4 selected clones (5F5, 6F10, 5A1 and 7A10) to find out whether the sorbitol promoter is able to produce human albumin (HA). The cell mass is developed and induction is carried out with three carbon sources such as Glucose, Methanol and Sorbitol. The shake flask induction samples are analysed using SDS PAGE, which is depicted in FIGS. 5, 6, 7 and 8. FIG. 5 represents the expression of Human albumin when cells are grown in the medium comprising sorbitol as a carbon source, wherein lane 1 relates to a protein molecular marker, lane 2 relates to *Pichia pastoris* with the sorbitol dehydrogenase promoter, lane 3, 4, 5, and 6 relates to HA in clones 5F5, 6F10, 5A1 and 7A10, respectively. Similarly, FIGS. 6, 7 relate to the expression of HA protein in *Pichia pastoris* when the cells are grown in the medium comprising methanol and glucose, respectively. FIG. 8 relates to expression analysis of cell free supernatant for the clones 5F5, 6F10, 5A1 and 7A10, where cells are grown in expansion medium without any induction Results and Conclusion:
a) The level of HA expression is good and it is found to be similar with all three carbon sources; sorbitol, methanol and glucose. The SDS PAGE band intensity obtained in all cases is equivalent to or more than 2 μgs, such band intensity is considered good expression.
b) Expression is observed during cell mass accumulation.
c) It also shows that the expression levels are increasing in dose dependent manner as it increases according to the higher G418 resistance as clone 5F5 is highest and 7A10 is the least among the clones selected.

Example 6: Expression of *Erythrina* Trypsin Inhibitor

In an attempt to find out the robustness of the Sorbitol dehydrogenase promoter for more number of heterologous protein expressions, *Erythrina* Trypsin Inhibitor (ETI) is been chosen. ETI is a small protein of ~20 KDa and it is useful for the affinity purification of Retaplase. The vector SDPHA/pMBL208 is digested with XhoI and EcoRI to remove HA gene from the vector. Synthetic ETI gene is subcloned into pMBL208 in place of HA gene. The ligated product is transformed to *E. coli* DH5α and plated on LBA100, plates are incubated overnight at 37° C. and the transformed colonies are screened for correct plasmid by colony PCR. The positive clone is isolated and inoculated in Luria Broth (LB) and grown overnight at 37° C. to isolate plasmid. The plasmid is isolated from overnight grown culture using Qiagen mini prep spin columns. Isolated plasmid is confirmed by restriction digestion with the following restriction enzymes—EcoRV/NdeI, EcoRV/EcoRI, EcoRI/NdeI and EcoRV. ETI gene is cloned into pMBL208 with and without sorbitol dehydrogenase promoter (FIGS. 9A and 9B). By doing so it is demonstrated that the production of ETI is due to the 210 bps sorbitol promoter and not because of any upstream promoter activity.

Example 7: Shake Flask Expression Studies

The plasmid SDPETI/pMBL208 is linearized with EcoRV and transformed to *P. pastoris*. The transformed cells are spread on to Yeast nitrogen base (YNB) agar plates without any amino acids for selection. The plates are incubated at 30° C. for two days till the colonies appear. Upon observing growth of the colonies in YNB agar plates, the colonies are picked and inoculated into Yeast Extract Peptone Dextrose (YPD) in 96-well plate and incubated at 30° C., overnight. The cultures from 96-well plate are stamped onto YPD agar plates containing 0.5 mg/ml of G418 and incubated the plated at 30° C. for 2 days. After 2 days the colonies showing higher resistance to G418 are selected and streaked onto YPD agar plates.

The clones selected based on the higher resistant to G418 are clones 1, 2, 3 and 4, these clones are inoculated into shake flask containing medium, expression of ETI in shake flask is analysed on 12% SDS PAGE (sodium dodecyl sulfate polyacrylamide gel electrophoresis). Productivity of expressed ETI under different carbon sources is shown in FIGS. 10 and 11, the arrow mark shows the expressed ETI on the gel.

Results and Conclusion:

Sorbitol dehydrogenase promoter is able to produces 20 kDa ETI when grown in any of the carbon sources such as sorbitol, glucose, glycerol, fructose, mannitol, sucrose, lactic acid, starch and methanol. No expression is found without the sorbitol promoter upsetream of ETI. The productivity of the expressed protein is found to be higher when Glycerol is used as a carbon source. Lactic acid also is been able to produce ETI when compared to other saccharides such as monosaccharide, disaccharide and polysaccharides when used as a carbon source.

A Comparative Expression status for the heterologous protein produced under the influence of Sorbitol dehydrogenase promoter is shown in table 1 below.

| Construct integrated into the *Pichia pastoris* genome | Inducer/ carbon source | Expression status |
| --- | --- | --- |
| Parent *Pichia pastoris* host | Methanol | No |
| ETI/pMBL208 (ETI CDS without SDP) | Methanol | No |
| SDPETI/pMBL208 (ETI CDS under SDP regulation) | Methanol | Yes |
| SDPETI/pMBL208 (ETI CDS under SDP regulation) | Glucose | Yes |
| SDPETI/pMBL208 (ETI CDS under SDP regulation | Sorbitol | Yes |
| SDPETI/pMBL208 (ETI CDS under SDP regulation | Glycerol | Yes |
| SDPHA/pMBL208 (Human albumin under SDP regulation) | Methanol | Yes |
| SDPHA/pMBL208 (Human albumin under SDP regulation) | Glucose | Yes |
| SDPHA/pMBL208 (Human albumin under SDP regulation) | Sorbitol | Yes |
| SDPHA/pMBL208 (Human albumin under SDP regulation) | Glycerol | Yes |

We claim:

1. A process of isolation of SEQ ID NO: 1, wherein said process comprising acts of:
   a) isolating genomic DNA from *P. pastoris*;
   b) amplifying a region comprising SEQ ID NO: 1 within the isolated genomic DNA, wherein the amplification of SEQ ID NO: 1 is carried out by forward primer set forth as SEQ ID NO: 2 and reverse primer set forth as SEQ ID NO: 3; and
   c) subjecting the amplified product to a conventional gel elution procedure to isolate said SEQ ID No.1.

2. A process of expressing a gene under regulation of SEQ ID NO: 1 in a medium comprising non-specific inducer, wherein said process comprising acts of:
   a) cloning said gene in an expression construct downstream to the SEQ ID NO: 1;
   b) transforming a host with the expression construct; and
   c) expressing the gene under the regulation of said SEQ ID NO: 1 in a medium comprising non-specific inducer for production of heterologous protein.

3. The process as claimed in claim 2, wherein said host is methylotrophic yeast.

4. The process as claimed in claim 2, wherein said heterologous protein is selected from a group comprising human albumin and *erythrina* trypsin inhibitor.

5. The process as claimed in claim 2, wherein the non-specific inducer is selected from a group comprising sorbitol, glucose, glycerol, fructose, mannitol, lactic acid, sucrose, starch, methanol or any combination thereof.

6. A vector comprising the nucleotide sequence set forth as SEQ ID NO: 1.

7. A transformed host cell comprising the vector as claimed in claim 6.

8. The process of claim 3, wherein said methylotrophic yeast is *P. pastoris*.

* * * * *